United States Patent [19]
Patterson

[11] Patent Number: 4,732,603
[45] Date of Patent: Mar. 22, 1988

[54] 1-ARYL-1,4-DIHYDRO-4-OXO-5-CARBOXYPYRIDAZINE DERIVATIVES AND THEIR USE AS PLANT GROWTH REGULATORS AND HYBRIDIZING AGENTS

[75] Inventor: Dennis R. Patterson, North Wales, Pa.

[73] Assignee: Rohm and Haas Company, Philadelphia, Pa.

[21] Appl. No.: 551,438

[22] Filed: Nov. 14, 1983

Related U.S. Application Data

[63] Continuation of Ser. No. 193,677, Oct. 3, 1980, abandoned.

[51] Int. Cl.$^4$ .................. A01N 43/58; C07D 237/24; C07D 309/38; C07B 49/00
[52] U.S. Cl. .......................... 71/92; 544/239
[58] Field of Search .............................. 544/239; 71/92

[56] References Cited

U.S. PATENT DOCUMENTS

| | | | |
|---|---|---|---|
| 2,454,742 | 11/1948 | Morgan | 260/250 |
| 2,835,671 | 5/1958 | Staehelin | 260/250 |
| 3,326,660 | 6/1967 | Reicheneder et al. | 71/92 |
| 3,555,026 | 1/1971 | Reicheneder et al. | 71/92 |
| 3,867,126 | 2/1975 | Kupelian | 71/92 |
| 3,953,445 | 4/1976 | Schonbeck et al. | 260/250 A |
| 4,011,220 | 3/1977 | Kropp et al. | 544/239 |
| 4,345,934 | 8/1982 | Fujimoto | 71/92 |

FOREIGN PATENT DOCUMENTS

| | | |
|---|---|---|
| 2808795 | 9/1978 | Fed. Rep. of Germany . |
| 762141 | 11/1956 | United Kingdom ................ 260/250 |

OTHER PUBLICATIONS

Morrison I. Boyd, "Organic Chemistry", 2nd ed. (1966), pp. 510, 638.
Wiley et al., *J. Amer. Chem. Soc.*, 78, 624 (1955).
Morgan, *J. Amer. Chem. Soc.*, 70, 2253 (1948).

*Primary Examiner*—Mark L. Berch
*Attorney, Agent, or Firm*—Polly E. Ramstad

[57] ABSTRACT

The invention relates to 1-aryl-1,4-dihydro-4-oxo-5-carboxypyridazine derivatives which are not only useful as plant growth regulators and hybridizing agents for cereal crops but possess the additional utility of having an improved margin of safety as concerns plant injury and seed quality.

8 Claims, No Drawings

1-ARYL-1,4-DIHYDRO-4-OXO-5-CARBOXYPYRIDAZINE DERIVATIVES AND THEIR USE AS PLANT GROWTH REGULATORS AND HYBRIDIZING AGENTS

This is a continuation of application Ser. No. 193,677, filed Oct. 3, 1980 and now abandoned.

BACKGROUND OF THE INVENTION

In the field of chemical hybridizing agents 1-aryl-1,4-dihydro-4-oxo-6-alkylpyridazine-3-carboxylic acids are highly active pyridazine type gametocides. Although these compounds are highly effective as chemical hybridizing agents they do possess the disadvantage of producing plant injury and poor seed quality when overdosed slightly above their effective dosage rate. The 5-carboxypyridazines of the present invention are unexpectedly safer chemical hybridizing agents since they do not have any adverse effects as regards the quality of seed or amount of plant injury at dosage rates far above what is required to produce maximum male sterility which allows for higher percent yields of hybrid seed produced.

SUMMARY OF THE INVENTION

This invention relates to 1-aryl-1,4-dihydro-4-oxo-5-carboxypyridazines of the formula

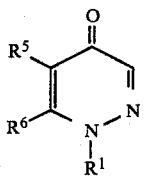

wherein $R^1$ is an aryl or alkyl group;

$R^5$ is a carboxy (COOH) group or the alkaline metal salt thereof, a carboalkoxy (COOR) group or a carboxamide (CONRR) group wherein R is an alkyl group and the agronomically acceptable acid addition salts thereof; and $R^6$ is an alkyl or aryl group.

The pyridazines of this type offer the advantage of causing less injury to treated plants while inducing male sterility thereby making them excellent plant growth regulators for use as cereal hybridizing agents.

As utilized in the present specification and claims, the term "aryl" is meant to include phenyl or naphthyl groups or phenyl or naphthyl groups substituted with up to three substituents selected from the group consisting of halogen, nitro, trihalomethyl, ($C_1$–$C_4$) alkoxy, ($C_1$–$C_4$) alkyl, and cyano. The term alkyl as utilized in the present specification and claims is meant to include alkyl groups of up to 4 carbon atoms which may be straight or branched chain alkyl groups.

A preferred embodiment of this invention relates to compounds of Formula (I) wherein $R^1$ is an aryl group substituted with up to three substituents selected from the group consisting of halogen, nitro, trihalomethyl, ($C_1$–$C_4$) alkoxy, ($C_1$–$C_4$) alkyl, and cyano; and $R^6$ is ($C_1$–$C_4$) alkyl group.

A more preferred embodiment of this invention relates to compounds of Formula I wherein $R^5$ is a carboxy (COOH) group or an alkali metal salt thereof, or a carbalkoxy (COOR) group wherein the group $R^5$ is an alkyl group of up to 4 carbon atoms and the agronomically acceptable acid addition salts thereof.

A most preferred embodiment of this invention relates to compounds according to Formula I wherein $R^1$ is a is a phenyl group substituted with up to two substituents selected from the group consisting of halogen, nitro trifluoromethyl, methoxy, methyl, and cyano, and $R^6$ is a methyl group or ethyl group.

Typical compounds which are encompassed by this invention include:

1-phenyl-1,4-dihydro-4-oxo-6-methylpyridazine-5-carboxylic acid 1-phenyl-1,4-dihydro-4-oxo-6-ethylpyridazine-5-carboxylic acid 1-phenyl-1,4-dihydro-4-oxo-6-propylpyridazine-5-carboxylic acid 1-phenyl-1,4-dihydro-4-oxo-6-butylpyridazine-5-carboxylic acid 1-phenyl-1,4-dihydro-4-oxo-6-benzylpyridazine-5-carboxylic acid 1-phenyl-1,4-dihydro-4-oxo-6-phenylpyridazine-5-carboxylic acid 1-(4-chlorophenyl)-1,4-dihydro-4-oxo-6-methylpyridazine-5-carboxylic acid 1-(4-bromophenyl)-1,4-dihydro-4-oxo-6-ethylpyridazine-5-carboxylic acid 1-(3,4-dichlorophenyl)-1,4-dihydro-4-oxo-6-propylpyridazine-5-carboxylic acid 1-(4-iodophenyl)-1,4-dihydro-4-oxo-6-butylpyridazine-5-carboxylic acid 1-(4-fluorophenyl)-1,4-dihydro-4-oxo-6-benzylpyridazine-5-carboxylic acid 1-(4-chlorophenyl)-1,4-dihydro-4-oxo-6-phenylpyridazine-5-carboxylic acid 1-(3-chlorophenyl)-1,4-dihydro-4-oxo-6-methylpyridazine-5-carboxylic acid 1-(2-chlorophenyl)-1,4-dihydro-4-oxo-6-ethylpyridazine-5-carboxylic acid 1-(3-bromophenyl)-1,4-dihydro-4-oxo-6-propylpyridazine-5-carboxylic acid 1-(2-bromophenyl)-1,4-dihydro-4-oxo-6-butylpyridazine-5-carboxylic acid 1-(2,4,6-trichlorophenyl)-1,4-dihydro-4-oxo-6-benzylpyridazine-5-carboxylic acid 1-(4-methylphenyl)-1,4-dihydro-4-oxo-6-phenylpyridazine-5-carboxylic acid 1-(4-trifluoromethylphenyl)-1,4-dihydro-4-oxo-6-methylpyridazine-5-carboxylic acid 1-(3-ethoxyphenyl)-1,4-dihydro-4-oxo-6-ethylpyridazine-5-carboxylic acid 1-(4-methylthiophenyl)-1,4-dihydro-4-oxo-6-propylpyridazine-5-carboxylic acid 1-(3-cyanophenyl)-1,4-dihydro-4-oxo-6-butylpyridazine-5-carboxylic acid 1-(2-chloro-4-methylphenyl)-1,4-dihydro-4-oxo-6-benzylpyridazine-5-carboxylic acid 1-(2-trifluoromethyl-4-chlorophenyl)-1,4-dihydro-4-oxo-6-methylpyridazine-5-carboxylic acid 1-(2-trifluoromethyl-4-bromophenyl)-1,4-dihydro-4-oxo-6-ethylpyridazine-5-carboxylic acid 1-(2-chloro-5-trifluoromethylphenyl)-1,4-dihydro-4-oxo-6-ethylpyridazine-5-carboxylic acid 1-(2-naphthyl)-1,4-dihydro-4-oxo-6-butylpyridazine-5-carboxylic acid and the agronomically acceptable alkali metal and acid addition salts thereof.

The following is a sequence utilized to prepare the compounds of the present invention.

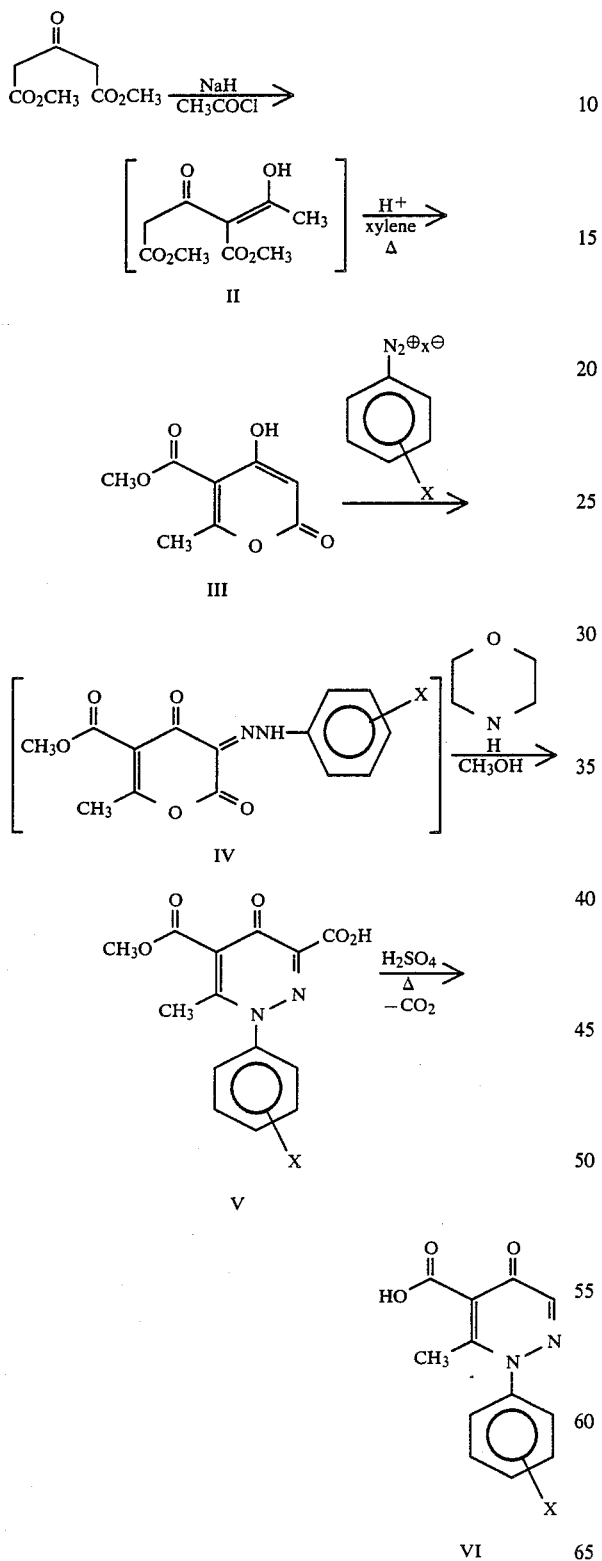

of either of these classes of compounds has been reported in the literature.

The compounds of Formula (V) are the subject of a copending patent application U.S. Ser. No. 193,672 filed Oct. 3, 1980 now abandoned after refiling as continuation Ser. No. 413,010, filed Aug. 30, 1982 by Dennis R. Patterson, which is assigned to a common assignee.

In the above reaction sequence a 3-oxoglutarate is first reacted with sodium hydride thereby replacing a hydrogen atom from the active methylene group followed by reaction with acetyl chloride to form the intermediate of Formula II which then rearranges under acid conditions to form the pyrone of Formula III. The pyrone is then reacted with a diazonium salt to form a hydrazone of Formula IV. The hydrazone is then rearranged in the presence of a base to form the dicarboxypyridazine of Formula V which is then decarboxylated under acidic conditions to form the 5-carboxypyridazine of Formula VI.

A more preferred synthetic route to the compounds of the present invention is outlined below.

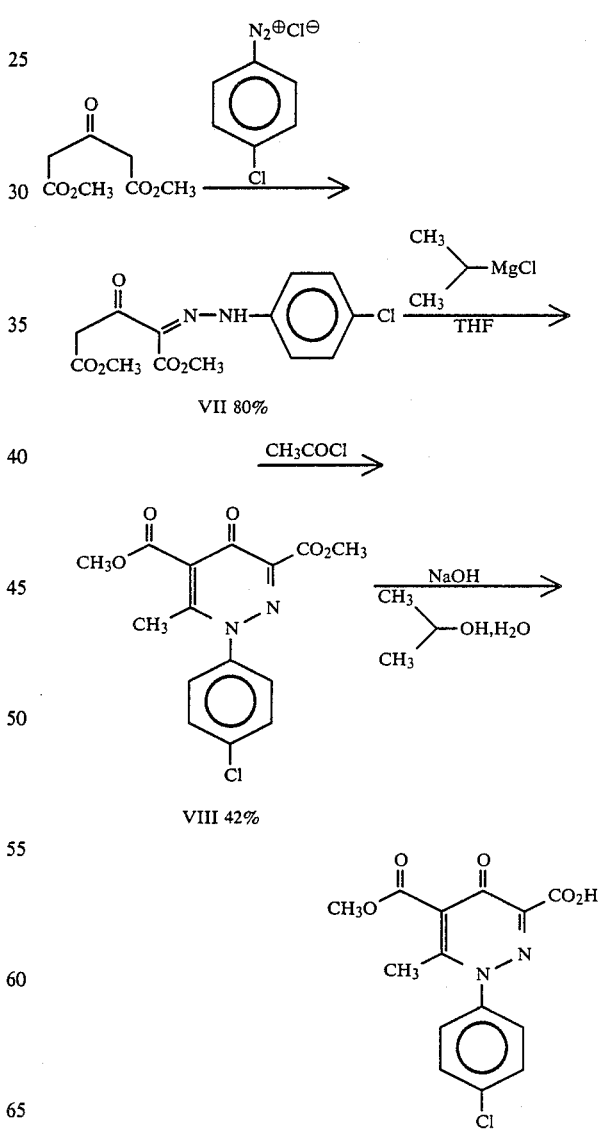

The synthetic sequence outlined above is unique in its ability to produce (V) and (VI). No directed syntheses In this approach the 3-oxoglutarate is first reacted with a diazonium salt to form the hydrazone of Formula VII which is then reacted with isopropyl magnesium chloride followed by reaction with acetyl chloride to form the dicarboxypyridazine ester of Formula VIII which is then hydrolyzed to the corresponding acid of Formula IX. Decarboxylation under strongly acidic conditions as above will again form the monocarboxy pyridazine of Formula VI.

The following examples are provided to illustrate the processes for preparing the compounds of the present invention. These examples are not to be considered in any way as being limitations on the breadth and scope of the present invention.

PROCESS A

Synthesis of 6-methyl-5-carbomethoxy-4-hydroxy-2-pyrone Via dimethyl-2-acetyl-3-oxoglutarate A 3-liter, three necked, round bottomed flask was equipped with addition funnel, paddle stirrer and thermometer. The flask was charged with 300 ml dry toluene and sodium hydride (50% as a dispersion in mineral oil, 82.8 g, 1.72 moles). The addition funnel was charged with dimethyl-3-oxoglutarate (dimethyl ester of acetone-1,3-dicarboxylic acid, 300 g, 1.72 moles). The flask was cooled to 5° in an ice-water bath. The diester was added dropwise to the sodium hydride slurry, not allowing the reaction temperature to exceed 10°. Complete addition required 3 hrs. The resulting mixture was stirred 30 min. at 5°. Acetyl chloride (135 g, 1.72 moles) was then added dropwise through the addition funnel, being careful to maintain the pot temperature at 5°–10°. After complete addition, the resulting slurry was stirred a further 30 min., then poured slowly into 500 ml water saturated with ammonium chloride. The resulting mixture showed a pH of 6. The layers were separated. The aqueous phase was extracted with methylene chloride (3×100 ml). The combined organic layers were taken to dryness in vacuo to leave a yellow oil. Vacuum distillation of this oil (at 0.5 mm Hg) gave fractions boiling from 50°–120°. A major fraction, bp 85°–110° (97 g) contained the desired acetylated diester, along with some starting material, as inferred by NMR.

The impure acetylated diester (97 g) obtained above, was dissolved in 300 ml dry xylene, along with p-toluenesulfonic acid (100 mg). This mixture was refluxed into a Dean-Stark trap for 12 hr. The resulting dark solution was cooled in an ice-water bath. The desired pyrone crystallizes out as fine needles (28.1 g, 10% yield based on dimethyl 3-oxoglutarate). An analytical sample was crystallized from ethyl acetate. NMR (CDCl$_3$): 5.6 ppm (S, 1H); 4.1 (S, 3H); 2.7 (S, 3H). IR (CH$_2$Cl$_2$): 5.75μ, 5.95, 6.90, 9.10. mp 104°–106°.

Elemental Analysis:
Expected: C: 52.18; H: 4.38. Found: C: 52.30; H: 4.44.

Synthesis of 1-(p-Chlorophenyl)-1,4-dihydro-4-oxo-3-carboxy-5-carbomethoxy-6-methylpyridazine A 250 ml, three necked, round bottomed flask was equipped with addition funnel, paddle stirrer, and thermometer. The flask was charged with 50 ml methanol, sodium acetate (16.0 g, 0.198 mole), and pyrone (8.0 g, 0.043 mole). p-Chlorobenzenediazonium chloride was prepared on the side by the dropwise addition of sodium nitrate (3.3 g, 0.047 mole) in 10 ml water to a cooled (5°) slurry containing p-chloroaniline (5.6 g, 0.043 mole) in aqueous hydrochloric acid (16.5 ml 12N HCl [0.198 mole] plus 10 ml water). The diazonium chloride solution was added dropwise to the solution containing the pyrone. This addition was carried out during 10 min. with no noticeable exotherm. After complete addition, the resulting orange slurry was stirred for 40 min. at room temperature. Suction filtration gave an orange filter cake which was washed repeatedly with water, then sucked dry during 2 hr. The filter cake thus obtained was placed back into the three necked flask used above. Methanol (200 ml) was added to give a slurry. Morpholine (10.0 g., 0.115 mole) was added in one portion. A mildly exothermic reaction occurred, and a dark, homogeneous solution was obtained. After stirring 10 min., the solution was poured into 300 ml water. This was extracted with methylene chloride (3×100 ml). The combined organic extracts were extracted repeatedly with dilute aqueous sodium hydroxide (pH 8). The combined aqueous basic layers were acidified with 6N hydrochloric acid. With cooling and scratching, a solid crystallized from solution. Suction filtration gave the product as a light brown powder (8.2 g, 60% yield based on the pyrone NMR (CDCl$_3$): 7.5 ppm (multiplet, 4H); 4.0 (S, 3H); 2.3 (S, 3H). IR (CH$_2$Cl$_2$): 5.75μ, 6.22, 6.90. mp 203°–204° (dec.). An analytical sample was crystallized from methanol.

Elemental Analysis:
Expected: C: 52.10; H: 3.44; N: 8.68. Found: C: 52.06; H: 3.43; N: 8.89.

Synthesis of 1-(p-Chlorophenyl)-1,4-dihydro-4-oxo-5-carboxy-6-methylpyridazine 1-(p-chlorophenyl)-1,4-dihydro-4-oxo-3-carboxy-5-carbomethoxy-6-methyl pyridazine (2.0 g, 6.2 mmoles) was dissolved in 10 ml, concentrated sulfuric acid, in an atmosphere of dry nitrogen. This was warmed rapidly to 200° and maintained there for 40 min. The resulting dark solution was cooled, then poured into cold water (5 ml). A brown precipitate formed immediately. Suction filtration and thorough washing with water gave the desired acid (1.0 g 63% yield), pure by NMR. NRM (CDCl$_3$): 8.5 ppm (S, 1H); 7.6 (AB quartet, 4H); 2.8 ppm (S, 3H). IR (Nujol): 5.81μ. mp 207°–208° (dec.).

An analytical sample was obtained by crystallization from methanol.

Elemental Analysis:
Expected: C: 54.45; H: 3.43; N: 10.59. Found: C: 54.45; H: 3.52; N: 10.16.

PROCESS B

Synthesis of Dimethyl-2,3-dioxyglutarate, 2-p-Chlorophenylhydrazone

A 10-liter widemouthed polyethylene container was fitted with a stirrer paddle and addition funnel. This container was charged with dimethyl-3-oxoglutarate (1 kg, 5.75 moles), methanol (1.5 l), and sodium acetate (1 kg, 12.19 moles). p-Chlorobenzenediazonium chloride (5.75 moles) was generated on the side in seven equal portions, by combining p-chloroaniline (7×104 g, 5.75 moles), hydrochloric acid (7×314 ml 12N, 26 moles), water (7×200 ml) and sodium nitrate (7×65.6 g in 100 ml H$_2$O, 6.66 moles). The diazonium salt was added dropwise, rapidly to the reaction kettle. The pH was monitored periodically and maintained at 5 during the course of the reaction by adding sodium acetate via spatula. At the end of the procedure, another 800 g of sodium acetate had been added. The resulting mixture was allowed to stand overnight, then suction filtered and the filter cake washed thoroughly with water. The brick-red filter cake was air dried to give 1.4 kg of the desired product (I) (80% yield). NMR (CDCl$_3$): 7.5 ppm (S, 4H); 3.9 ppm (S, 6H); 3.7 ppm (S, 2H). This compound is known to the literature. See: Bulow and Hopfner, Berichte, 34, 71 (1901); ibid, 44, 2835 (1911).

Synthesis of Dimethyl-1-(p-chlorophenyl)-1,4-dihydro-4-oxo-3,5-dicarboxylate A dry 1-liter, four-necked round bottomed flask was fitted with stirrer, thermometer, nitrogen inlet, and rubber septum. The flask was charged with dimethyl-2,3-dioxyglutarate, 2-p-chlorophenyl hydrazone (50 g, 0.16 mole) in dry tetrahydrofuran (170 ml). This solution was maintained under an atmosphere of dry nitrogen while cooling to 5° C. Isopropyl magnesium chloride (72 ml, 2.55N in ethyl ether, 0.16 mole) was added dropwise via syringe, maintaining the pot temperature at 5°-10° C. After complete addition, the mixture was stirred for 15 min. in the cold, then acetyl chloride (12 ml, 13.0 g, 0.16 mole) was added dropwise, rapidly, keeping the temperature of the reaction mixture below 10° C. The resulting dark solution was allowed to warm to room temperature during 2 hrs. Water (200 ml) was added. This mixture was stirred for 30 min., then extracted with ethyl acetate. The extracts were dried over MgSO$_4$, then filtered and reduced in volume in vacuo. The resulting dark oil was dissolved in ethyl ether, and cooled in an ice bath. The desired diester crystallized out to give 22.1 g yellow powder (42% yield), mp 153°-54° C. NMR (CDCl$_3$): 7.6 ppm (multiplet, 4H); 4.0 ppm (S, 6H); 2.3 ppm (S, 3H). IR (CH$_2$Cl$_2$): 5.75μ, 6.12, 9.15.

Table I below gives the structure, melting point and elemental analysis for some of the more representative compounds encompassed by the present invention which were prepared by the processes discussed above.

TABLE I

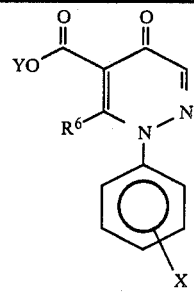

| Ex. No. | X | Y | R$^6$ | mp (°C.)$^a$ | | C | H | N |
|---|---|---|---|---|---|---|---|---|
| 1 | 4-Cl | Na | n-Butyl | 157–58° | Calcd | 58.73 | 4.93 | 9.13 |
| | | | | | Found | 58.91 | 4.84 | 9.25 |
| 2 | 4-Cl | Na | n-Propyl | 171–72° | Calcd | 57.44 | 4.48 | 9.57 |
| | | | | | Found | 57.43 | 4.33 | 9.30 |
| 3 | 3,4-diCl | Na | ethyl | 202–03° | Calcd | 49.86 | 3.22 | 8.95 |
| | | | | | Found | 50.12 | 3.27 | 9.32 |
| 4 | H | Na | ethyl | 163–64° | Calcd | 63.92 | 4.95 | 11.47 |
| | | | | | Found | 63.90 | 4.89 | 11.81 |
| 5 | 4-Cl | Na | ethyl | 190–191° | Calcd | 56.02 | 3.98 | 10.05 |
| | | | | | Found | 55.93 | 3.98 | 9.96 |
| 6 | 4-Br | Na | ethyl | 220° (dec) | Calcd | 48.32 | 3.43 | 8.67 |
| | | | | | Found | 48.71 | 3.45 | 8.66 |
| 7 | H | Na | methyl | 204° (dec) | Calcd | 62.60 | 4.38 | 12.17 |
| | | | | | Found | 63.05 | 4.47 | 11.94 |
| 8 | 4-Cl | ethyl | methyl | 175–77° | Calcd | 57.44 | 4.48 | 9.57 |
| | | | | | Found | 57.17 | 4.66 | 9.55 |
| 9 | 4-F | Na | methyl | 211–12° | Calcd | 58.06 | 3.65 | 11.29 |
| | | | | | Found | 57.69 | 3.70 | 11.11 |
| 10 | 4-Cl | methyl | methyl | 140–42° | Calcd | 56.02 | 3.98 | 10.05 |
| | | | | | Found | 55.78 | 4.06 | 10.00 |
| 11 | 3,4-diCl | Na | methyl | 213–14° | Calcd | 48.18 | 2.69 | 9.37 |
| | | | | | Found | 47.52 | 2.72 | 4.74 |
| 12 | 4-Br | Na | methyl | 200–10° (dec) | Calcd | 46.62 | 2.93 | 9.06 |
| | | | | | Found | 46.74 | 2.91 | 9.32 |
| 13 | 4-Cl | Na | methyl | 207–08° | Calcd | 54.45 | 3.43 | 10.59 |
| | | | | | Found | 54.45 | 3.52 | 10.16 |
| 14 | 4-Cl | ethyl | ethyl | 129–131° | Calcd | 58.73 | 4.93 | 9.13 |
| | | | | | Found | 58.61 | 5.12 | 9.26 |
| 15 | 4-Cl | methyl | ethyl | 119–20° | Calcd | 57.44 | 4.48 | 9.57 |
| | | | | | Found | 57.18 | 4.49 | 9.76 |
| 16 | 4-I | Na | ethyl | 185–86° | Calcd | 43.35 | 3.08 | 7.78 |
| | | | | | Found | 41.40 | 2.94 | 7.59 |
| 17 | 2-Cl | Na | ethyl | 174–75° | Calcd | 56.02 | 3.98 | 10.05 |
| | | | | | Found | 55.99 | 3.91 | 10.43 |

$^a$Melting Points and Elemental Analyses recorded are for the parent acid of the sodium salts.

The compounds of the invention are particularly useful as chemical hybridization agents in cereal crops, such as wheat, barley, corn, rice sorghum, millets, oats, rye, triticale, forage crops and the like. When used as chemical hybridization agents, the compounds effectively induce a high degree of selective male sterility, without also inducing significant female sterility, in the treated plants and without causing significant growth inhibition of the treated plants. As used herein, the term male sterility includes both actual male sterility, as evidenced by a lack of male flower parts or by sterile pollen, and functional male sterility, in which the male flower parts are unable to cause pollination. The compounds of the invention also cause other plant growth regulatory responses, such as, for example, control of flowering, control of fruiting and inhibition of seed formation in non-cereal species and other related growth regulatory responses.

When used as plant growth regulators, the compounds of the invention are applied in any amount which will be sufficient to effect the desired plant response without causing any undesirable or phytotoxic response. For example, when the compounds of the invention are used as chemical hybridization agents, they are generaly applied to the crops to be treated at a rate of about 1/32 to about 20 pounds per acre and preferably about ⅛ to about 10 pounds per acre. The rate of application will vary depending on the crop being treated, the compound being used for treatment, and related factors.

To obtain hybrid seed, the following procedure is generally employed. The two parents to be crossed are planted in alternate strips. The female parent is treated with a compound of the invention. The male-sterile female parent thus produced will be pollinated by pollen from the other, male-fertile, male parent, and the seed produced by the female parent will be hybrid seed which can then be harvested by conventional means.

A preferred method of applying a compound of the invention as a chemical hybridization agent is by foliar application. When this method is employed, selective male sterility is most effectively induced when the compound is applied between flower-initiation and meiosis. The compounds of the inventions may also be applied as a seed treatment by soaking the seed in a liquid formulation containing the active compound or by coating the seed with the compound. In seed treatment applications, the compounds of the invention will generally be applied at a rate of about ¼ to about 10 pounds per hundred weight of seed. The compounds of the invention are also effective when applied to the soil or to the water surface in rice crops.

The compounds of the invention can be used as plant growth regulators either individually or in mixtures. For example, they can be used in combination with other plant growth regulators, such as auxins, gibberellins, ethylene-releasing agents such as ethephon, pyridones, cytokinins, maleic hydrazide, succinic acid 2,2-dimethylhydrazide, choline and its salts, (2-chloromethyl)trimethylammonium chloride, triiodobenzoic acid, tributyl-2,4-dichlorobenzylphosphonium chloride, polymeric N-vinyl-2-oxazolidinones, tri(dimethylaminoethyl)phosphate and its salts, and N-dimethylamino-1,2,3,6-tetrahydrophthalamic acid and its salts, and the like, and under some conditions may be used advantageously with other agricultural chemicals such as herbicides, fungicides, insecticides, and plant bactericides.

A compound of the invention can be applied to the growth medium or to plants to be treated either by itself or, as is generally done, as a component in a growth regulant composition or formulation which also comprises an agronomically acceptable carrier. By "agronomically acceptable carrier" is meant any substance which can be used to dissolve, disperse, or diffuse a compound in the composition without impairing the effectiveness of the compound and which by itself has no significant detrimental effect on the soil, equipment, crops, or agronomic environment. Mixtures of the compounds of the invention may also be used in any of these formulations. The compositions of the invention can be either solid or liquid formulations or solutions. For example, the compounds can be formulated as wettable powders, emulsifiable concentrates, dusts, granular formulations, aerosols, or flowable emulsion concentrates. In such formulations, the compounds are extended with a liquid or solid carrier and, when desired suitable surfactants are incorporated.

It is usually desirable, particularly in foliar applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds of the invention can be dissolved in any appropriate solvent. Examples of solvents which are useful in the practice of this invention include water, alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% by weight with a preferred range being about 20% to about 75%.

For the preparation of emulsifiable concentrates, the compound can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent or surfactant which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates of usually about 10% to 60% by weight and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98% by weight, preferably about 40% to 75%. A dispersing agent may generally constitute about 0.5% to about 3% by weight of the composition, and a wetting agent may generally constitute from about 0.1% to about 5% by weight of the composition.

Dusts can be prepared by mixing the compounds of the invention with finely divided inert solids which may be organic or inorganic in nature. Materials used for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% by weight use concentrations.

Granular formulations can be prepared by impregnating a solid such as granular fuller's earth, vermiculite, ground corn cobs, seed hulls, including bran or other grain hulls, or similar material. A solution of one or more of the compounds in a volatile organic solvent can be sprayed or mixed with the granular solid and the solvent then removed by evaporation. The granular material can have any suitable size, with a preferably size range of 16 to 60 mesh. The active compound will usually comprise about 2 to 15% by weight of the granular formulation.

Salts of the compounds of the invention can be formulated and applied as aqueous solutions. The salt will typically comprise about 0.05 to about 50% by weight, preferably about 0.1% to about 10%, of the solution. These compositons can also be further diluted with water if desired prior to actual application. In some applications, the activity of these compositions can be enhanced by incorporating into the composition an adjuvant such as glycerin, methylethylcellulose, hydroxyethylcellulose, polyoxyethylenesorbitan monooleate, polypropylene glycol, polyacrylic acid, polyethylene sodium malate, polyethylene oxide, or the like. The adjuvant will generally comprise about 0.1 to about 5% by weight, preferably about 0.5 to about 2%, of the composition. Such compositions can also optionally include an agronomically-acceptable surfactant.

The compounds of the invention can be applied as sprays by methods commonly employed, such as conventional hydraulic sprays, aerial sprays, and dusts. For low-volume applications a solution of the compound is usually used. The dilution and volume of application will usually depend upon such factors as the type of equipment employed, the method of application, the area to be treated and the type and stage of the development of the crop being treated.

The following example will further illustrate the growth regulatory activity of the compounds of the invention but are not intended to limit the invention in any way.

EXAMPLE 18

Chemical Hybridization Activity

The following procedures are used to evaluate the activity of the compounds of the invention for inducing male sterility in cereals.

An awned variety (Fielder) and an awnless variety (May-64) of spring wheat are planted at the rate of 6 to 8 seeds per 6 inch pot containing a sterile medium of 3 parts soil and 1 part humus. The plants are grown under short-day (9 hour) conditions for the first 4 weeks to obtain good vegatative growth before flower initiation. The plants are then moved to long-day (16 hour) conditions which are provided by high intensity lights in the greenhouse. The plants are fertilized at 2, 4, and 8 weeks after planting with a water soluble fertilizer (16-25-16) at the rate of 1 tsp/gal of water, and are frequently sprayed with isotox for aphid control and dusted with sulfur for powdery mildew control.

Test compounds are foliarly applied to the awned female plants when these plants reach the flag leaf emergence stage (stage 8 on Feekes' scale). All compounds are applied in a carrier volume of 50 gal/A containing a surfactant, such as Triton ® X-100 surfactant at the rate of 2 oz/50 gal.

After spike emergence but before anthesis, 4 to 6 spikes per pot are bagged to prevent outcrossing. At the first signs of the flower opening, two spikes per pot are cross pollinated, using the approach method, with the awnless male parent. As soon as the seeds become plainly visible, spike length is measured and seeds per spikelet counted in both bagged and crossed spikes. Male sterility can then be calculated as percent inhibition of seed set in bagged spikes of treated plants, and female fertility in crossed spikes can be calculated as percent of control seed set. After maturity the seed on crossed spikes are planted for determination of percent hybridization.

Percent sterility, percent fertility, and percent height inhibition are calculated from the following formulas:

a. % Sterility = $(S_c - S_t/S_c) \times 100$
   $S_c$ = seeds/spikelet in bagged spikes of control plants.
   $S_t$ = seeds/spikelet in bagged spikes of treated plants.

b. % Fertility = $(F_t/F_c) \times 100$
   $F_t$ = seeds/spikelet in approach crossed spikes of treated plants
   $F_c$ = seeds/spikelet in unbagged spikes of control plants c. % Height inhibition = $(H_c - H_t/H_c) \times 100$
   $H_c$ = Height of control plants
   $H_t$ = Height of treated plants Table II summarizes typical results obtained in the evaluation of compounds of the invention. A dash indicates that no determination of value was made.

TABLE II

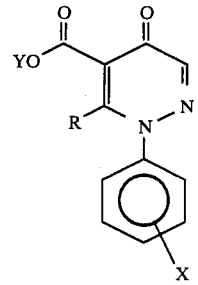

| Ex. | Rate (#Acre) | Sterility % | Injury (0-9) |
|---|---|---|---|
| 1 | ⅛ | 0 | 0 |
|   | ¼ | 24.4 | 0 |
|   | ½ | 74.2 | 0 |
|   | 1 | 91.0 | 0 |
|   | 2 | 99.1 | 0 |
| 2 | ⅛ | 0 | 0 |
|   | ¼ | 29.4 | 0 |
|   | ½ | 75.1 | 0 |
|   | 1 | 99.1 | 0 |
|   | 2 | 100 | 0 |
| 3 | ¼ | 5.7 | 0 |
|   | ½ | 57.9 | 0 |
|   | 2 | 99.1 | 0 |
|   | 8 | 100 | 0 |
| 4 | ¼ | 3.1 | 0 |
|   | ½ | 26.6 | 0 |
|   | 2 | 46.9 | 0 |
|   | 8 | 55.3 | 0 |
| 5 | ½ | 77.0 | 0 |
|   | 1 | 98.0 | 0 |
|   | 2 | 100.0 | 0 |
|   | 8 | 100.0 | 0 |
| 6 | ¼ | 20.0 | 0 |

TABLE II-continued

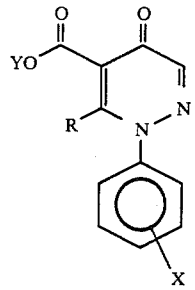

| Ex. | Rate (#Acre) | Sterility % | Injury (0-9) |
|---|---|---|---|
|  | ½ | 82.0 | 0 |
|  | 2 | 99.0 | 0 |
|  | 8 | 100.0 | 0 |
| 7 | ⅛ | 0 | 0 |
|  | ½ | 28.0 | 0 |
|  | 2 | 100.00 | 0 |
|  | 8 | 100.0 | 0 |
| 8 | 1 | 6.0 | 0 |
|  | 2 | 4.0 | 0 |
|  | 4 | 5.0 | 0 |
|  | 8 | 3.0 | 0 |
| 9 | 1 | 66.0 | 0 |
|  | 2 | 72.0 | 0 |
|  | 4 | 100.0 | 0 |
|  | 8 | 100.0 | 0 |
| 10 | 1 | 10.0 | 0 |
|  | 2 | 3.0 | 0 |
|  | 4 | 8.0 | 0 |
|  | 8 | 8.0 | 0 |
| 11 | ½ | 2.0 | 0 |
|  | 1 | 0 | 0 |
|  | 2 | 0 | 0 |
|  | 4 | 16.0 | 0 |
| 12 | ½ | 1.0 | 0 |
|  | 1 | 0 | 0 |
|  | 2 | 0 | 0 |
|  | 4 | 57.0 | 0 |
| 13 | 1 | 99.0 | 0 |
|  | 2 | 100.0 | 0 |
|  | 4 | 100.0 | 0 |
|  | 8 | 100.0 | 0 |
| 14 | ¼ | 0.8 | 0 |
|  | ½ | 0 | 0 |
|  | 1 | 0 | 0 |
|  | 2 | 6.0 | 0 |
| 15 | ¼ | 10.8 | 0 |
|  | ½ | 39.4 | 0 |
|  | 1 | 90.8 | 0 |
|  | 2 | 100.0 | 1 |
| 16 | ¼ | 19.9 | 0 |
|  | ½ | 41.2 | 0 |
|  | 1 | 90.5 | 0 |
|  | 2 | 93.2 | 0 |
| 17 | ⅛ | 4.2 | 0 |
|  | ½ | 7.0 | 0 |
|  | 2 | 27.1 | 0 |
|  | 8 | 14.0 | 0 |

The 5-carboxypyridazinones of the present invention exhibit an improved margin of safety while maintaining the levels of activity as compared to the 3-carboxypyridazones.

Greenhouse data on the 1-aryl-1,4-dihydro-4-oxo-6-alkylpyridazine-5-carboxylic acids of the present invention as compared to 1(p-chlorophenyl)-1,4-dihydro-4-oxo-6-methylpyridazone-3-carboxylic acid, a known compound, are presented in Table III.

TABLE III

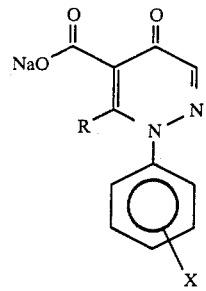

| X | R | Dosage (#/acre) | Sterility | Injury |
|---|---|---|---|---|
| H | $CH_3CH_2-$ | ⅛ | 3.1% | 0 |
|  |  | ½ | 26.6% | 0 |
|  |  | 2 | 46.9% | 0 |
|  |  | 8 | 55.3% | 0 |
| 3,4-diCl | $CH_3CH_2-$ | ⅛ | 5.7% | 0 |
|  |  | ½ | 57.9% | 0 |
|  |  | 2 | 99.1% | 0 |
|  |  | 8 | 100.0% | 0 |
| 4-Cl | $CH_3CH_2-$ | ⅛ | 77.0% | 0 |
|  |  | ½ | 98.0% | 0 |
|  |  | 2 | 100.0% | 0 |
|  |  | 8 | 100.0% | 0 |
| 4-Br | $CH_3CH_2-$ | ⅛ | 20.0% | 0 |
|  |  | ½ | 82.0% | 0 |
|  |  | 2 | 99.0% | 0 |
|  |  | 8 | 100.0% | 0 |
| H | $CH_3$ | ⅛ | 0 | 0 |
|  |  | ½ | 28.0% | 0 |
|  |  | 2 | 100.0% | 0 |
|  |  | 8 | 100.0% | 0 |

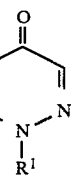

| | | ¼ | 78.0% | 0 |
|---|---|---|---|---|
| | | ½ | 96.0% | 0 |
| | | 1 | 100.0% | 1 |
| | | 2 | 100.0% | 5 |

The improved safety margin of the 5-carboxypyridazinones relative to the known 1-(p-chlorophenyl)-1,4-dihydro-4-oxo-6-methylpyridazine-3-carboxylic acid also makes them effective cereal breeding tools when applied directly to the seed of the female parent before planting.

It is to be understood that changes and variations of the subject matter of this invention may be made without departure from the spirit of the invention as defined by the appended claims.

I claim:

1. A compound of the formula wherein $R^1$ is 4-Cl-$C_6H_4$; $R^5$ is $CO_2Na$ or $CO_2K$; and $R^6$ is $CH_3$ or $C_2H_5$.

2. The compound of claim 1 wherein $R^1$ is 4-Cl-$C_6H_4$; $R^5$ is $CO_2Na$; and $R^6$ is $CH_3$.

3. The compound of claim 1 wherein $R^1$ is 4-Cl-$C_6H_4$; $R^5$ is $CO_2Na$; and $R^6$ is $C_2H_5$.

4. The compound of claim 1 wherein $R^1$ is 4-Cl-$C_6H_4$; $R^5$ is $CO_2K$; and $R^6$ is $C_2H_5$.

5. A method for inducing male sterility in a cereal grain plant which comprises treating the plant prior to meiosis with a compound of claim 1 in an amount from about 0.125 to about 10 pounds per acre, which amount is effective to produce male sterility in the plant.

6. A composition for inducing male sterility in cereal grain plants which comprises an effective amount of a compound of claim 1 and an agronomically acceptable carrier.

7. A method for producing hybrid cereal grain seed comprising treating a female parent of the cereal grain prior to meiosis with a compound of claim 1 in an amount of from 0.125 to about 8 pounds per acre which amount induces male sterility in the female plant, pollinating the female parent with pollen from a different plant which is a different line from the female plant, allowing the female parent to produce seed and collecting the produced hybrid seed.

8. The method of claim 7 wherein the cereal grain is wheat.

* * * * *